(12) United States Patent
Arai et al.

(10) Patent No.: US 10,354,833 B2
(45) Date of Patent: Jul. 16, 2019

(54) SAMPLE HOLDER, FIXING MEMBER AND METHOD FOR FIXING SAMPLE

(71) Applicant: Shimadzu Corporation, Kyoto (JP)

(72) Inventors: Hiroshi Arai, Kyoto (JP); Akinori Kogure, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/966,537

(22) Filed: Apr. 30, 2018

(65) Prior Publication Data

US 2018/0330914 A1    Nov. 15, 2018

(30) Foreign Application Priority Data

May 15, 2017   (JP) ................. 2017-096736

(51) Int. Cl.
| | | |
|---|---|---|
| G01N 1/31 | (2006.01) | |
| G01Q 30/14 | (2010.01) | |
| G01Q 60/00 | (2010.01) | |
| G02B 21/34 | (2006.01) | |
| H01J 37/20 | (2006.01) | |

(52) U.S. Cl.
CPC ............. *H01J 37/20* (2013.01); *G01N 1/31* (2013.01); *G01Q 30/14* (2013.01); *G01Q 60/00* (2013.01); *G02B 21/34* (2013.01)

(58) Field of Classification Search
CPC .......... H01J 37/20; G01N 1/31; G01Q 30/14; G01Q 60/00; G02B 21/34
USPC ..................... 250/306, 307, 440.11
See application file for complete search history.

(56) References Cited

FOREIGN PATENT DOCUMENTS

JP        5510400 B2     6/2014

*Primary Examiner* — Nicole M Ippolito
*Assistant Examiner* — Hanway Chang
(74) *Attorney, Agent, or Firm* — Maier & Maier, PLLC

(57) ABSTRACT

A sample holder includes a sample container and a fixing member. The fixing member is inserted into the sample container in a state in which a sample is placed, and fixes the sample by sandwiching the sample between the fixing member and a bottom surface of the sample container. At this time, a peripheral edge portion of the fixing member is elastically deformed by being inserted into the sample container, and the fixing member sandwiches the sample by its elastic force. Therefore, even when the sample is placed in the sample container in the state of being immersed in a liquid, the sample can be held in a stable state by the fixing member.

6 Claims, 8 Drawing Sheets

SAMPLE HOLDER, FIXING MEMBER AND METHOD FOR FIXING SAMPLE

FIELD

The present invention relates to a sample holder and a fixing member used in a scanning probe microscope which performs measurement by relatively moving a probe along a surface of a sample, and a sample fixing method for fixing a sample in the scanning probe microscope.

BACKGROUND

From related art, a scanning probe microscope has been used as an apparatus which inspects a fine surface shape of a sample. In the scanning probe microscope, by relatively moving the probe to the surface of the sample and scanning the probe, a change in a physical quantity (such as a tunnel current or an interatomic force) acting between the probe and the sample surface during scanning is detected. Further, by performing a feedback-control of the relative position of the probe to keep the physical quantity constant during scanning, the surface shape of the sample can be measured on the basis of the feedback amount.

When observing the sample using such a scanning probe microscope, it is necessary to dispose the sample in a stable state in order to prevent the sample from moving during observation. From this point, for example, the sample is set at an observation position in a state of being held in a dedicated sample container (see, for example, Patent Literature 1 below).

In the fixing method described in the following Patent Literature 1, by applying an adhesive to a groove provided in a sample container, and by disposing a sample in the sample container in that state, the sample is fixed to the sample container by adhesion. Further, the sample container of the state in which the sample is fixed is set on the stage of the scanning probe microscope, and observation of the sample is performed.

As a result, observation can be performed in a state in which the sample is fixed.
[Patent Literature 1] Japanese Patent No. 5510400

SUMMARY

However, in the above-described fixing method, when observing the sample immersed in a solution, there was a problem of difficulty in fixing the sample. Specifically, since the sample is immersed in the solution, the adhesive may be dissolved. In this case, the sample cannot be fixed to the sample container with the adhesive, and the sample moves during observation. As a result, it adversely affects the observation of the sample.

The invention has been made in view of the above circumstances, and an object thereof is to provide a sample holder capable of holding a sample in a stable state even when the sample is immersed in a liquid.

(1) A sample holder according to the invention is used in a scanning probe microscope which performs measurement by relatively moving a probe along a surface of a sample. The sample holder includes a sample container and a fixing member. The sample container has an insertion hole, and the sample can be inserted into the sample container from the insertion hole. The fixing member is inserted into the sample container from the insertion hole and fixes the sample by sandwiching the sample between the fixing member and an inner surface of the sample container. When the fixing member is inserted into the sample container, a peripheral edge portion is elastically deformed, the fixing member holds the sample by an elastic force thereof, and an opening section for exposing the surface of the sandwiched sample is formed.

According to such a configuration, when the fixing member is inserted into the sample container in a state in which the sample is inserted into the sample container, the peripheral edge portion of the fixing member is elastically deformed, and the fixing member sandwiches the sample between the peripheral edge portion and the inner surface of the sample container by the elastic force.

Therefore, even in a case where the sample is placed in the sample container while being immersed in the liquid, the sample can be held in a stable state.

Further, in the fixing member, the opening section for exposing the surface of the sample is formed.

Therefore, the sample can be observed via the opening section, while keeping the sample in a fixed state.

(2) Further, by bending the peripheral edge portion of the fixing member, a spring plate section is formed, and by elastic deformation of the spring plate section, the fixing member may sandwich the sample by the elastic force.

According to such a configuration, the spring plate section can be easily configured in the fixing member.

(3) Further, a plurality of notches may be formed in the peripheral edge portion of the fixing member, and a plurality of spring plate sections may be formed by the plurality of notches.

According to such a configuration, the spring plate section can be more easily configured in the fixing member.

(4) A fixing member according to the invention is used in a scanning probe microscope which performs measurement by relatively moving a probe along a surface of a sample, and sandwiches and fixes the sample between the fixing member and an inner surface of a sample container. The fixing member includes an opening section and a spring plate section. The opening section exposes the surface of the sandwiched sample. The spring plate section is formed by bending a peripheral edge portion.

(5) Further, a plurality of notches may be formed in the peripheral edge portion of the fixing member, and a plurality of spring plate sections may be formed by the plurality of notches.

(6) A sample fixing method according to the invention is for fixing a sample in a scanning probe microscope which performs measurement by relatively moving a probe along a surface of the sample. The sample fixing method includes a sample installing step and a sample fixing step. In the sample installing step, the sample is installed in a sample container having an insertion hole in a state of being immersed in a liquid. In the sample fixing step, a fixing member is inserted into the interior of the sample container from the insertion hole to immerse the fixing member in the liquid, the sample is sandwiched and fixed between the fixing member and an inner surface of the sample container, and the surface of the sample is exposed from an opening section formed in the fixing member. In the sample fixing step, when the fixing member is inserted into the sample container, a peripheral edge portion of the fixing member is elastically deformed, and the sample is held by an elastic force.

According to the invention, when the fixing member is inserted into the sample container in a state in which the sample is inserted in the sample container, the peripheral edge portion of the fixing member is elastically deformed, and the fixing member sandwiches the sample between the peripheral edge portion and the inner surface of the sample container by the elastic force. Therefore, even in a case where the sample is placed in the sample container while being immersed in the liquid, the sample can be held in a stable state.

BRIEF DESCRIPTION OF THE DRAWINGS

FIG. 4 (*b*) is a diagram for describing a method for fixing a sample using the sample holder;

FIG. 4 (*c*) is a diagram for describing a method for fixing a sample using the sample holder;

DETAILED DESCRIPTION OF THE DRAWINGS

1. Sample Holder

Figure 1:
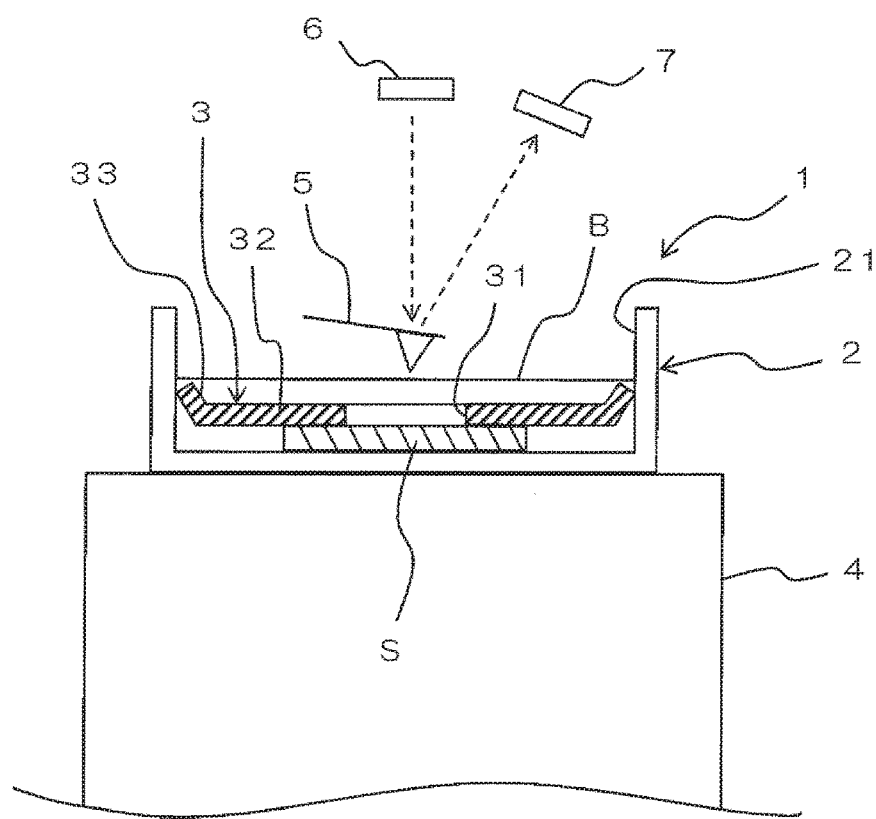
FIG. 1 is a schematic diagram illustrating a configuration example of a sample holder according to a first embodiment of the invention.

FIG. 1 is a schematic diagram illustrating a configuration example of a sample holder according to a first embodiment of the invention.

A sample holder 1 is a member for holding a sample observed with a scanning probe microscope, and includes a sample container 2 and a fixing member 3.

The sample container 2 is made of, for example, a resin material. The sample container 2 is formed in a cylindrical shape with a closed lower end, and extends in a vertical direction. That is, an upper end of the sample container 2 is open. An inner space of the upper end portion of the sample container 2 is an insertion hole 21.

The fixing member 3 is a member used by being inserted into the sample container 2, and is formed in a disc shape. An outer diameter of the fixing member 3 is slightly larger than an inner diameter of the sample container 2. A peripheral edge portion of the fixing member 3 is configured to be elastically deformable. The fixing member 3 has an opening section 31 formed therein. The detailed configuration of the fixing member 3 will be described later.

When observing the sample, the sample container 2 is placed on a stage 4 of the scanning probe microscope. Further, in the sample container 2, a sample S and the fixing member 3 are disposed, and a liquid B is stored. In the sample container 2, the sample S and the fixing member 3 are immersed in the liquid B, and the fixing member 3 is disposed above the sample S. Therefore, the sample S is fixed in the sample container 2 by the fixing member 3, without being exposed to the atmosphere.

In this way, the sample S is observed in a state in which the sample holder 1 which holds the sample S is placed on the stage 4 of the scanning probe microscope.

The scanning probe microscope in which the sample holder 1 is set is, for example, an atomic force microscope (AFM), and includes the stage 4, a cantilever 5, a light source 6, a light-receiving unit 7, and the like.

For example, a piezoelectric element (not illustrated) is attached to an outer peripheral surface of the stage 4. By applying a voltage to the piezoelectric element, the stage 4 is appropriately deformed, and the position of the sample S on the stage 4 changes.

The cantilever 5 is, for example, an elongated member supported in a cantilever manner, and a probe is provided at a leading end portion on a free end side. The cantilever 5 (a probe of the cantilever 5) is scanned along a surface of the sample S via the opening section 31 of the fixing member 3.

The light source 6 is configured to emit laser beam.

The light-receiving unit 7 is, for example, a photodiode or the like, and is configured to receive and detect the reflected light from the cantilever 5.

In the scanning probe microscope, when observing the sample S, the stage 4 is appropriately deformed with the sample holder 1 set on the stage 4, and the position of the sample S on the stage 4 changes. As a result, the probe of the cantilever 5 is relatively moved with respect to the surface of the sample S and is scanned along the surface of the sample S. During the scanning, an interatomic force acting between the probe and the surface of the sample S changes.

Further, laser beam is irradiated from the light source 6. Light from the light source 6 is directed to the probe of the cantilever 5. Further, the light (reflected light) reflected by the probe of the cantilever 5 is received by the light-receiving unit 7.

Since the probe of the cantilever 5 is relatively moved along the unevenness of the surface of the sample S, the probe is deflected depending on the shape of the unevenness. When the probe of the cantilever 5 is deflected, the position at which the reflected light is received changes in the light-receiving unit 7. Therefore, it is possible to detect a change in the interatomic force acting between the probe of the cantilever 5 and the surface of the sample S during the scanning, on the basis of the change in the light-receiving position of the reflected light in the light-receiving unit 7. Further, the surface shape of the sample S is measured by operating the stage 4 on the basis of the change in the interatomic force.

In this way, when observing the sample S with the scanning probe microscope, the sample S is fixed by the sample holder 1. That is, the sample S is kept in a state of being disposed at a fixed position in the sample container 2. Therefore, the sample S can be accurately observed.

2. Detailed Configuration of Fixing Member

Figure 2:
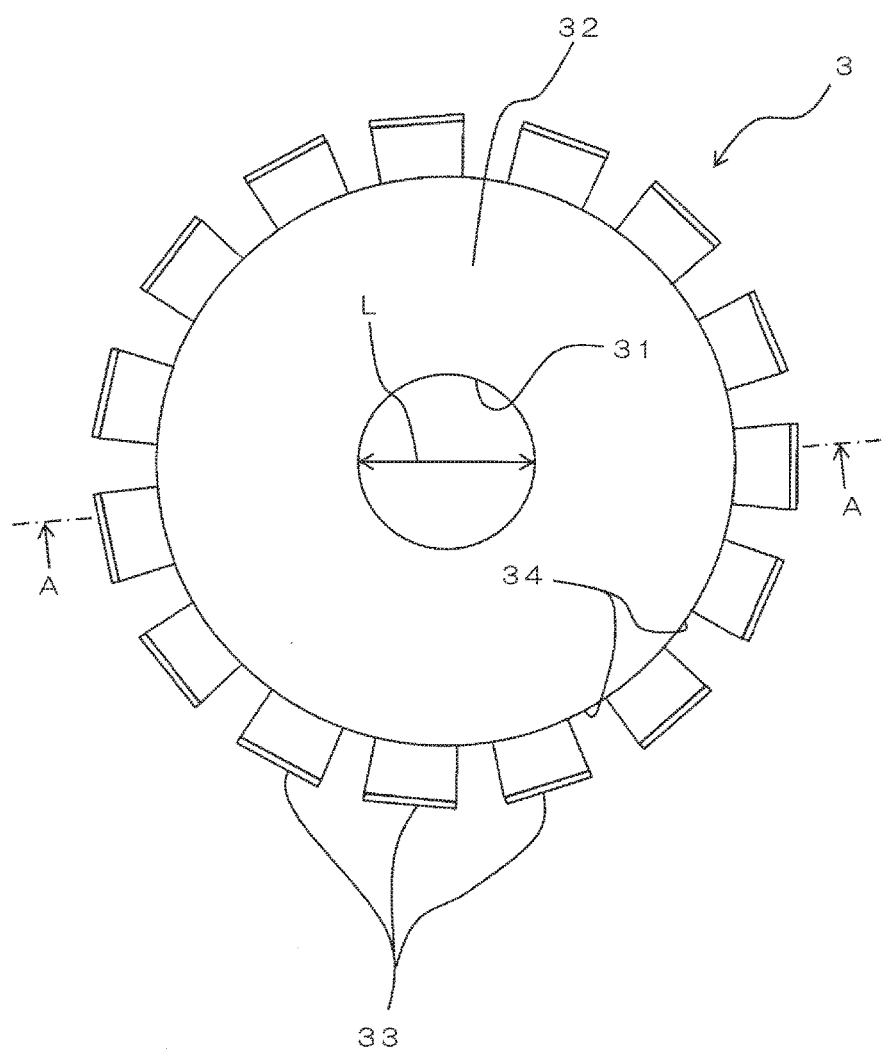
FIG. 2 is a plan view illustrating a fixing member of FIG. 1.
Figure 3:
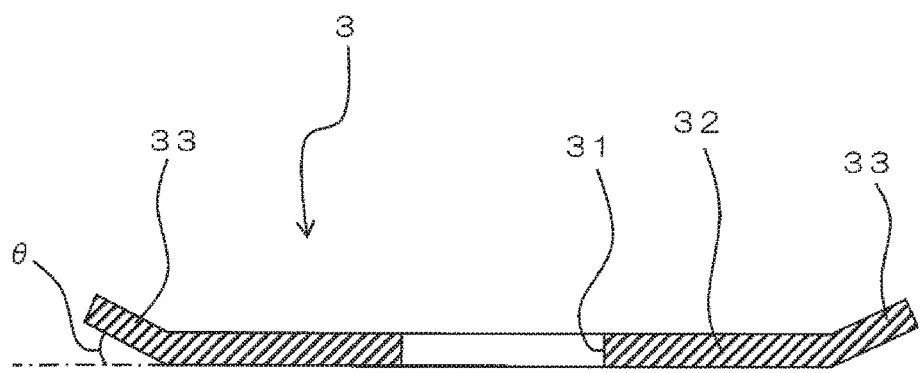
FIG. 3 is a cross-sectional view taken along line A-A of FIG. 2.

FIG. 2 is a plan view illustrating the fixing member 3. FIG. 3 is a cross-sectional view taken along line A-A of FIG. 2.

The fixing member 3 is made of, for example, a resin material such as polyethylene terephthalate (PET). The fixing member 3 includes a flat plate section 32 and a plurality of spring plate sections 33.

The flat plate section 32 is formed in a flat disc shape. The above-described opening section 31 is formed in a central portion of the flat plate section 32. The opening section 31 has a circular shape in a plan view, and penetrates the flat plate section 32 in a thickness direction. An inner diameter L of the opening section 31 is about ⅓ of the diameter of the flat plate section 32 and is larger than a scanning width of the cantilever 5 of the scanning probe microscope. Specifically, the inner diameter L of the opening section 31 is, for example, 10 mm.

The spring plate section 33 is formed in a flat plate shape having a rectangular shape in a plan view, and protrudes outward from the outer peripheral edge of the flat plate section 32. Specifically, the spring plate section 33 is inclined to face one side in the thickness direction from the outer peripheral edge of the flat plate section 32 toward an outer side in a radial direction. As illustrated in FIG. 3, an angle θ formed between a direction along the spring plate section 33 and a direction along the flat plate section 32 is less than 90°. As illustrated in FIG. 2, the plurality of spring plate sections 33 are disposed at equal intervals along a circumferential direction of the flat plate section 32. A region between the respective spring plate sections 33 is a notch 34.

When manufacturing the fixing member 3, first, a member is prepared in a state in which the plurality of spring plate sections 33 protrude in a horizontal direction from the outer peripheral edge of the flat plate section 32 (in a non-inclined state). That is, a disk-like member having a diameter larger than the diameter of the flat plate section 32 and having a plurality of notches 34 formed in a peripheral edge portion thereof is prepared. Further, the fixing member 3 is manufactured (configured) by bending the peripheral edge portion (the spring plate section 33 extending in the horizontal direction) of the member at the angle θ.

3. Fixation of Sample Using Sample Holder

Figure 4:
FIG. 4 (*a*) is a diagram for describing a method for fixing a sample using the sample holder.
Figure 4:
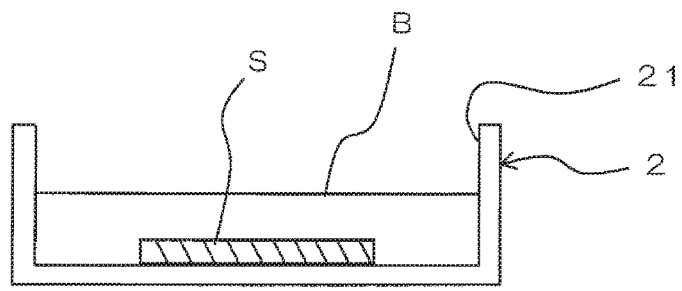
Figure 4:
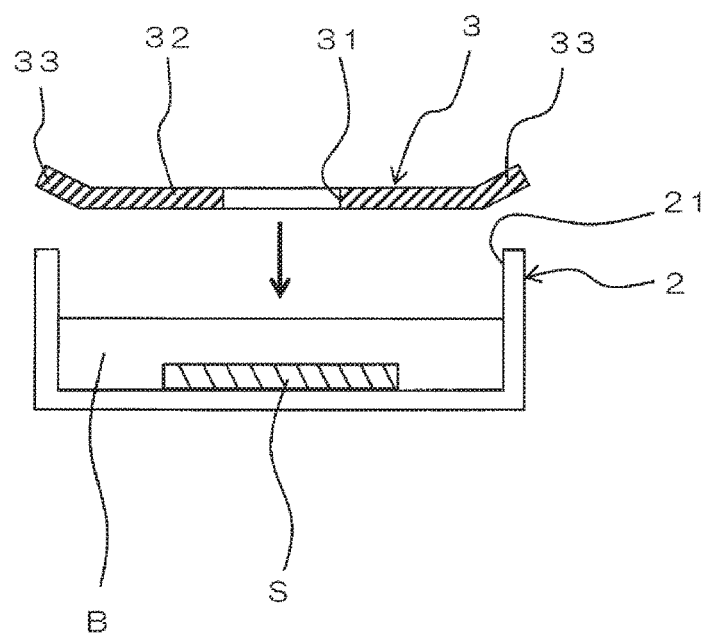

FIGS. 4 (*a*)-4 (*c*) are diagrams for describing a method for fixing the sample S using the sample holder 1. When fixing the sample S in the scanning probe microscope, a user first prepares the sample container 2 as illustrated in FIG. 4(*a*).

Further, as illustrated in FIG. 4 (*b*), the user introduces the sample S and the liquid B into the sample container 2 from the insertion hole 21. That is, the user installs the sample S in the sample container 2 in the state of being immersed in the liquid B (a sample installing step). At this time, after placing the sample S in the sample container 2, the user may introduce the liquid B into the sample container 2, or after introducing the liquid B into the sample container 2, the user may introduce the sample S into the sample container 2.

Thereafter, as illustrated in FIG. 4(*c*), the user moves the fixing member 3 downward from the upper part of the sample container 2 and inserts the fixing member 3 into the sample container 2 from the insertion hole 21. At this time, the user inserts the fixing member 3 into the sample container 2 until the fixing member 3 is immersed in the liquid B and the lower surface of the fixing member 3 abuts against the sample S.

As described above, the outer diameter of the fixing member 3 is larger than the inner diameter of the sample container 2. Therefore, when the fixing member 3 is inserted into the sample container 2, first, the spring plate section 33 of the fixing member 3 comes into contact with the upper end portion of the sample container 2.

When the fixing member 3 is further inserted into the sample container 2 from this state, the spring plate section 33 of the fixing member 3 elastically deforms so as to be further bent upward, by contact with the sample container 2. Further, the fixing member 3 comes into contact with the sample S in a state in which the spring plate section 33 is elastically deformed (further bent). The fixing member 3 is fixed inside the sample container 2 by friction with the inner wall of the sample container 2. Further, as illustrated in FIG. 1, the user places the sample container 2 and the fixing member 3 of this state on the stage 4.

As a result, the sample S is sandwiched between the fixing member 3 (the flat plate section 32) and the sample container 2 (the bottom wall of the sample container 2) by the elastic force of the spring plate section 33 (a sample fixing step). In this state, the surface (upper surface) of the sample S is exposed from the opening section 31.

In this manner, the sample S is held between the fixing member 3 and the bottom surface (inner surface) of the sample container 2 by the elastic force of the fixing member 3 in a state of being immersed in the liquid B inside the sample container 2. Therefore, it is possible to fix the sample S in a state of being immersed in the liquid B, without using an adhesive or the like.

When observation of the sample S in the scanning probe microscope is completed, the fixing member 3 is detached from the sample container 2. At this time, the user grips and lifts the spring plate section 33 of the fixing member 3, for example, with tweezers or the like, thereby detaching the fixing member 3 from the inside of the sample container 2. That is, the spring plate section 33 of the fixing member 3 also functions as a holding section for gripping the fixing member 3.

In this way, the fixing member 3 can easily fix the sample S in the sample container 2, and can easily detach the sample from the fixing member 3.

The fixing member 3 detached from the inside of the sample container 2 can be used (reusable) again as the sample holder 1 at the time of subsequent observation using the scanning probe microscope. Depending on the type of liquid B introduced into the sample container 2, the sample container 2 is discarded without being reused.

4. Operational Effect (1) According to the present embodiment, as illustrated in FIG. 1, the sample holder 1 includes the sample container 2 and the fixing member 3. The fixing member 3 is inserted into the sample container 2 in a state in which the sample S is placed, and fixes the sample S by sandwiching the sample S between the fixing member 3 and the bottom surface of the sample container 2. At this time, as the fixing member 3 is inserted into the sample container 2, the peripheral edge portion (spring plate section 33) is elastically deformed, and the sample S is sandwiched by the elastic force (a sample fixing step).

Therefore, even when the sample S is placed in the sample container 2 in the state of being immersed in the liquid B, the sample S can be held in a stable state by the fixing member 3.

The opening section 31 for exposing the surface of the sample S is formed on the flat plate section 32 of the fixing member 3.

Therefore, the sample can be observed via the opening section 31, while keeping the sample S in a fixed state.

(2) According to the present embodiment, as illustrated in FIGS. 2 and 3, the peripheral edge portion of the fixing member 3 is bent to form the spring plate section 33. When the fixing member 3 is inserted into the sample container 2, since the spring plate section 33 of the fixing member 3 is elastically deformed, the sample S is sandwiched by the elastic force thereof.

Therefore, the spring plate section 33 can be easily formed in the fixing member 3.

5. Second Embodiment

Hereinafter, another embodiment of the invention will be described with reference to FIGS. 5 to 8. The same configurations and methods as those in the first embodiment are denoted by the same reference numerals as those described above, and the description thereof will not be provided. In the following another embodiment, a configuration of a fixing member that can be used in place of the fixing member 3 will be described. The shapes of the following respective fixing members are different from that of the fixing member 3.

Figure 5:
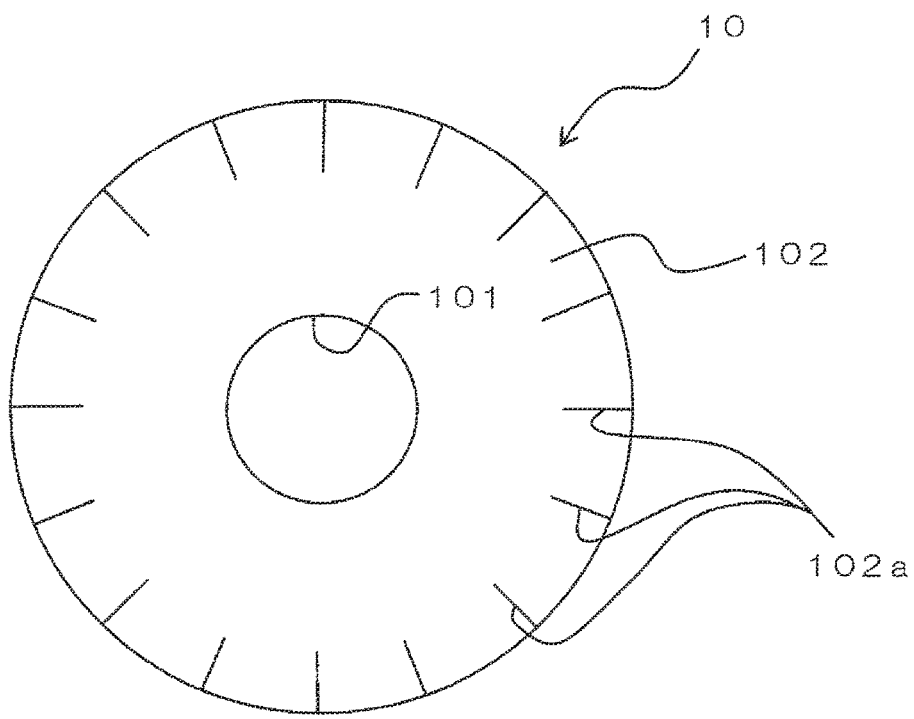
FIG. 5 is a plan view illustrating a fixing member of a sample holder according to a second embodiment of the invention.

FIG. 5 is a plan view illustrating a fixing member 10 of the sample holder 1 according to the second embodiment of the invention.

In the sample holder 1 of the second embodiment, the fixing member 10 is used.

The fixing member 10 is formed in a disc shape. An opening section 101 having a circular shape in a plan view is formed at the center of the fixing member 10. In a peripheral edge portion 102 of the fixing member 10, a plurality of notches 102a is formed. The notches 102a are formed to extend along the radial direction. The plurality of notches 102a are arranged at equal intervals in the circumferential direction.

In the fixing member 10, the peripheral edge portion 102 is bent toward one side in the thickness direction. The peripheral edge portion 102 bent in this way functions as a spring plate section. Further, in FIG. 5, the fixing member 10 in a state before the peripheral edge portion 102 is bent is illustrated.

When the fixing member 10 is inserted into the sample container 2, the peripheral edge portion 102 is elastically deformed so as to be further bent.

As described above, according to the second embodiment, in the fixing member 10, the notches 102a are formed in the peripheral edge portion 102 of the fixing member 10 formed in a disc shape. Further, in the fixing member 10, the peripheral edge portion 102 is bent toward one side in the thickness direction, and the bent peripheral edge portion 102 functions as a spring plate section.

Therefore, in the fixing member 10, the peripheral edge portion 102 (spring plate section) can be more easily configured.

6. Third Embodiment

Figure 6:
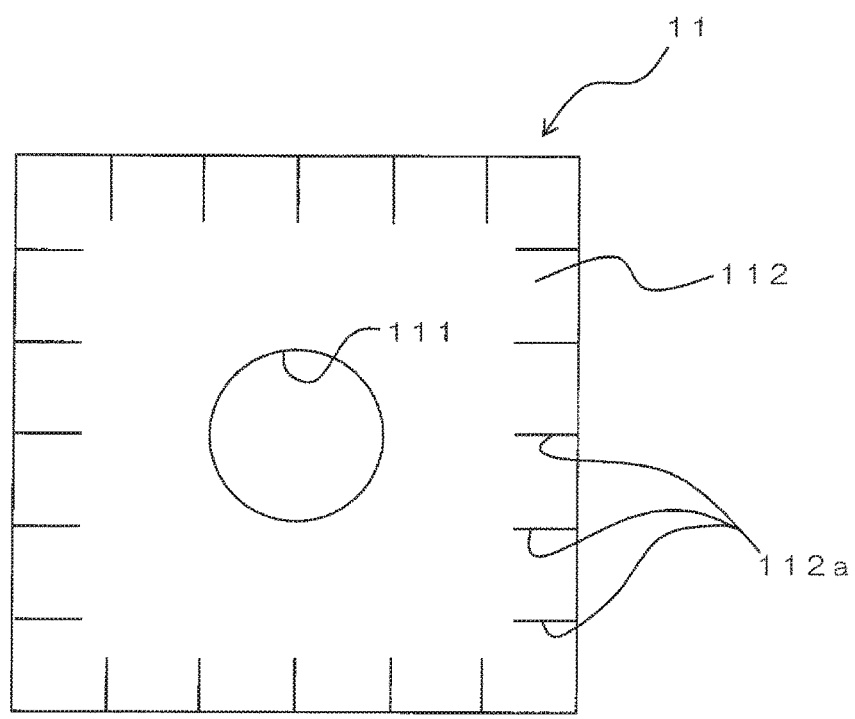
FIG. 6 is a plan view illustrating a fixing member of a sample holder according to a third embodiment of the invention.

FIG. 6 is a plan view illustrating a fixing member 11 of the sample holder 1 according to the third embodiment of the invention.

In the sample holder 1 of the third embodiment, the fixing member 11 is used.

The fixing member 11 is formed in a plate shape having a rectangular shape in a plan view. An opening section 111 having a circular shape in a plan view is formed at the center of the fixing member 11. A plurality of notches 112a is formed in a peripheral edge portion 112 of the fixing member 11. The notches 112a are formed along a direction orthogonal to the outer edge of the peripheral edge portion 112. The plurality of notches 112a are arranged at equal intervals in the direction along the outer edge of the peripheral edge portion 112.

In the fixing member 11, the peripheral edge portion 112 is bent toward one side in the thickness direction. The peripheral edge portion 112 bent in this way functions as a spring plate section. In FIG. 6, the fixing member 11 in a state before the peripheral edge portion 112 is bent is illustrated.

When the fixing member 11 is inserted into the sample container 2, the peripheral edge portion 112 is elastically deformed so as to be further bent.

In this way, according to the third embodiment, in the fixing member 11, the notches 112a are formed in the peripheral edge portion 112 of the plate-like fixing member 11 having a rectangular shape in a plan view. Further, in the fixing member 11, the peripheral edge portion 112 is bent toward one side in the thickness direction, and the bent peripheral edge portion 112 functions as a spring plate section.

Therefore, in the fixing member 11, the peripheral edge portion 112 (spring plate section) can be more easily configured.

7. Fourth Embodiment

Figure 7:
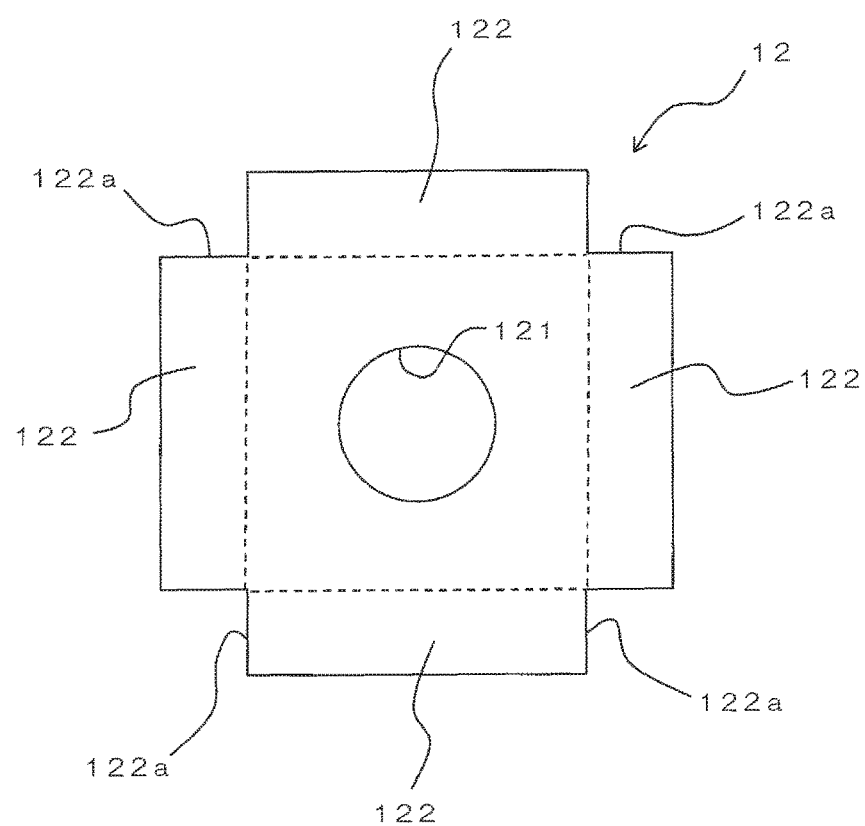
FIG. 7 is a plan view illustrating a fixing member of a sample holder according to a fourth embodiment of the invention.

FIG. 7 is a plan view illustrating a fixing member 12 of the sample holder 1 according to the fourth embodiment of the invention.

In the sample holder 1 of the fourth embodiment, the fixing member 12 is used.

The fixing member 12 has a plate shape having a rectangular shape in a plan view, and is formed in a shape in which corners are notched. At the center of the fixing member 12, an opening section 121 having a circular shape in a plan view is formed. A notch 122a is formed at each corner of a peripheral edge portion 122 of the fixing member 12. The notch 122a is formed in a rectangular shape in a plan view.

In the fixing member 12, the peripheral edge portion 122 is bent toward one side in the thickness direction. The peripheral edge portion 122 bent in this way functions as a spring plate section. Further, in FIG. 7, the fixing member 12 in a state before the peripheral edge portion 122 is bent is illustrated.

Further, when inserting the fixing member 12 into the sample container 2, the peripheral edge portion 122 is elastically deformed so as to be further bent.

In this way, according to the fourth embodiment, the fixing member 12 has a plate shape of a rectangular shape in a plan view, and is formed in a shape in which the corners are notched. Further, in the fixing member 12, the peripheral edge portion 122 is bent toward one side in the thickness direction, and the bent peripheral edge portion 122 functions as a spring plate section.

Therefore, in the fixing member 12, the peripheral edge portion 122 (spring plate section) can be more easily configured.

8. Fifth Embodiment

Figure 8:
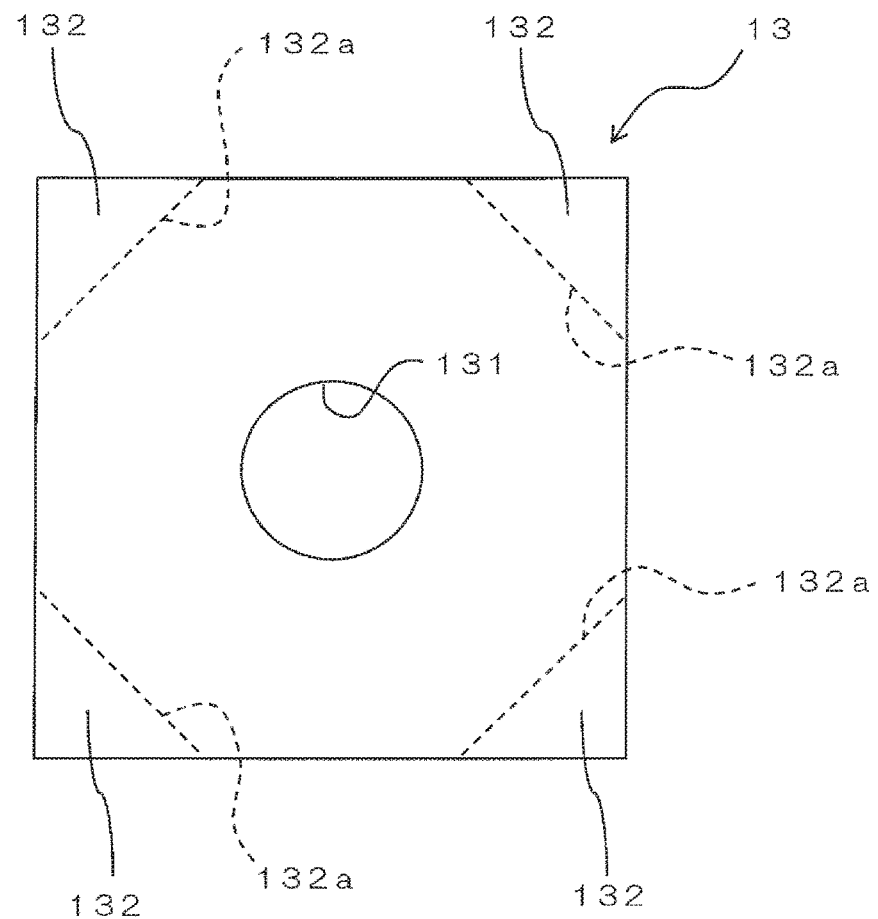
FIG. 8 is a plan view illustrating a fixing member of a sample holder according to a fifth embodiment of the invention.

FIG. 8 is a plan view illustrating a fixing member 13 of the sample holder 1 according to a fifth embodiment of the invention.

In the sample holder 1 of the fifth embodiment, the fixing member 13 is used.

The fixing member 13 is formed in a plate shape having a rectangular shape in a plan view. At the center of the fixing member 13, an opening section 131 having a circular shape in a plan view is formed. Each corner 132 which is a part of a peripheral edge portion of the fixing member 13 is bent toward one side in the thickness direction with a bending line 132a as a boundary. The corner 132 bent in this way functions as a spring plate section. In FIG. 8, the fixing member 13 in a state before the corner 132 is bent is illustrated.

When the fixing member 13 is inserted into the sample container 2, the corner 132 is elastically deformed so as to be further bent.

In this way, according to the fifth embodiment, in the fixing member 13, the corner 132 of the plate-like fixing member 13 having a rectangular shape in a plan view is bent toward one side in the thickness direction, and the bent corner 132 functions as a spring plate section.

Therefore, in the fixing member 13, the corner 132 can easily function as a spring plate section.

9. Modified Example

In the above embodiments, the sample container 2 has been described as being formed in a cylindrical shape with closed lower end. However, the sample container 2 may be formed in a rectangular tube shape with closed lower end. Further, the sample container 2 may be formed in a tubular shape having an elliptical shape in a plan view with closed lower end.

Further, in the above embodiments, each fixing member has been described as being inserted into the sample container 2 in a state in which the peripheral edge portion is bent in advance. However, each of the fixing members may be inserted into the sample container 2 in a state in which the peripheral edge portion thereof is not bent, and may be elastically deformed so that the peripheral edge portion is bent from that state.

Further, in the aforementioned embodiments, the cantilever 5 and the sample S have been described as being relatively moved by deforming the stage 4 in the scanning probe microscope. However, in the scanning microscope, the cantilever 5 may be moved with respect to the sample S, without deforming the stage 4.

Further, in the above embodiments, the fixing member 3 has been described as being made of PET. However, the fixing member 3 may be another resin such as polyethylene (PE) and polystyrene (PS). Further, the fixing member 3 is not limited to resin, and may be metal or the like. However, for example, when the liquid B is acid, alkali, electrolytic solution or the like, it is preferable that the fixing member 3 be a resin which is hard to react with the liquid B.

Further, in the above embodiment, the fixing member 3 has been described as having a circular shape or a rectangular shape in a plan view. However, the shape of the fixing member 3 in a plan view can be any shape such as an elliptical shape, a triangular shape, a polygonal shape, and a star shape.

The invention claimed is:

1. A sample holder used in a scanning probe microscope which performs measurement by relatively moving a probe along a surface of a sample, the sample holder comprising:
a sample container having an insertion hole, the sample being insertable into the sample container from the insertion hole; and
a fixing member which is inserted into the sample container from the insertion hole and fixes the sample by sandwiching the sample between the fixing member and an inner surface of the sample container,
wherein, when the fixing member is inserted into the sample container, a peripheral edge portion is elastically deformed, the fixing member holds the sample by an elastic force thereof, and an opening section for exposing the surface of the sandwiched sample is formed.

2. The sample holder according to claim 1, wherein, by bending the peripheral edge portion of the fixing member, a spring plate section is formed, and by elastic deformation of the spring plate section, the fixing member sandwiches the sample by the elastic force.

3. The sample holder according to claim 2, wherein a plurality of notches is formed in the peripheral edge portion of the fixing member, and a plurality of spring plate sections is formed by the plurality of notches.

4. A fixing member which is used in a scanning probe microscope which performs measurement by relatively moving a probe along a surface of a sample, the fixing member sandwiching and fixing the sample between the fixing member and an inner surface of a sample container, the fixing member comprising:
an opening section for exposing the surface of the sandwiched sample; and
a spring plate section formed by bending a peripheral edge portion.

5. The fixing member according to claim 4, wherein a plurality of notches is formed in the peripheral edge portion, and a plurality of spring plate sections is formed by the plurality of notches.

6. A sample fixing method for fixing a sample in a scanning probe microscope which performs measurement by relatively moving a probe along a surface of the sample, the method comprising:
a sample installing step of installing the sample in a sample container having an insertion hole in a state of being immersed in a liquid;
a sample fixing step of inserting a fixing member into the interior of the sample container from the insertion hole to immerse the fixing member in the liquid, sandwiching and fixing the sample between the fixing member and an inner surface of the sample container, and exposing the surface of the sample from an opening section formed in the fixing member,
wherein in the sample fixing step, when the fixing member is inserted into the sample container, a peripheral edge portion of the fixing member is elastically deformed, and the sample is held by an elastic force.

* * * * *